United States Patent [19]

Strube

[11] Patent Number: 5,789,399

[45] Date of Patent: Aug. 4, 1998

[54] TREATMENT OF PRURITUS WITH VITAMIN D AND ANALOGS THEREOF

[76] Inventor: Marilyn E. Strube, 1017 Olive St., Belleville, Ill. 62220

[21] Appl. No.: 720,698

[22] Filed: Oct. 2, 1996

Related U.S. Application Data

[60] Provisional application No. 60/005,030 Oct. 10, 1995.

[51] Int. Cl.$^6$ ..................................................... A61K 31/59
[52] U.S. Cl. ............................................................. 514/167
[58] Field of Search ............................................... 514/167

[56] References Cited

U.S. PATENT DOCUMENTS

| | | | |
|---|---|---|---|
| 3,711,602 | 1/1973 | Herschler | 424/45 |
| 4,416,886 | 11/1983 | Bernstein | 424/260 |
| 5,057,500 | 10/1991 | Thornfeldt | 514/53 |
| 5,190,935 | 3/1993 | Binderup et al. | 514/167 |
| 5,342,833 | 8/1994 | Doran et al. | 514/167 |
| 5,362,719 | 11/1994 | Godtfredsen | 514/167 |
| 5,374,629 | 12/1994 | Calverley et al. | 514/167 |

OTHER PUBLICATIONS

Blachley et al., Uremic Pruritus: Skin Divalant Ion Content and Response to Ultraviolet Phototherapy. *Am. J. Kidney Dis.* 5:237–241, 1985.

Martindale, *The Extra Pharmacopoeia 30th Ed.*, Martindale, 1993, pp. 1058–1059.

The Merck Index (11th Ed.) Budavari et al., Merck & Co., Inc., Rahway, N.J. (1989) p. 1206.

*Primary Examiner*—Marianne M. Cintins
*Assistant Examiner*—M. Moezie
*Attorney, Agent, or Firm*—Howell & Haferkamp, L.C.

[57] ABSTRACT

A method for treating pruritus comprising topical administration of formulation of vitamin D or an analog of vitamin D is disclosed. The formulation comprises a therapeutically effective, water-based emulsion, water-based suspension or oil-based formulation of vitamin D or analog of vitamin D.

7 Claims, 1 Drawing Sheet

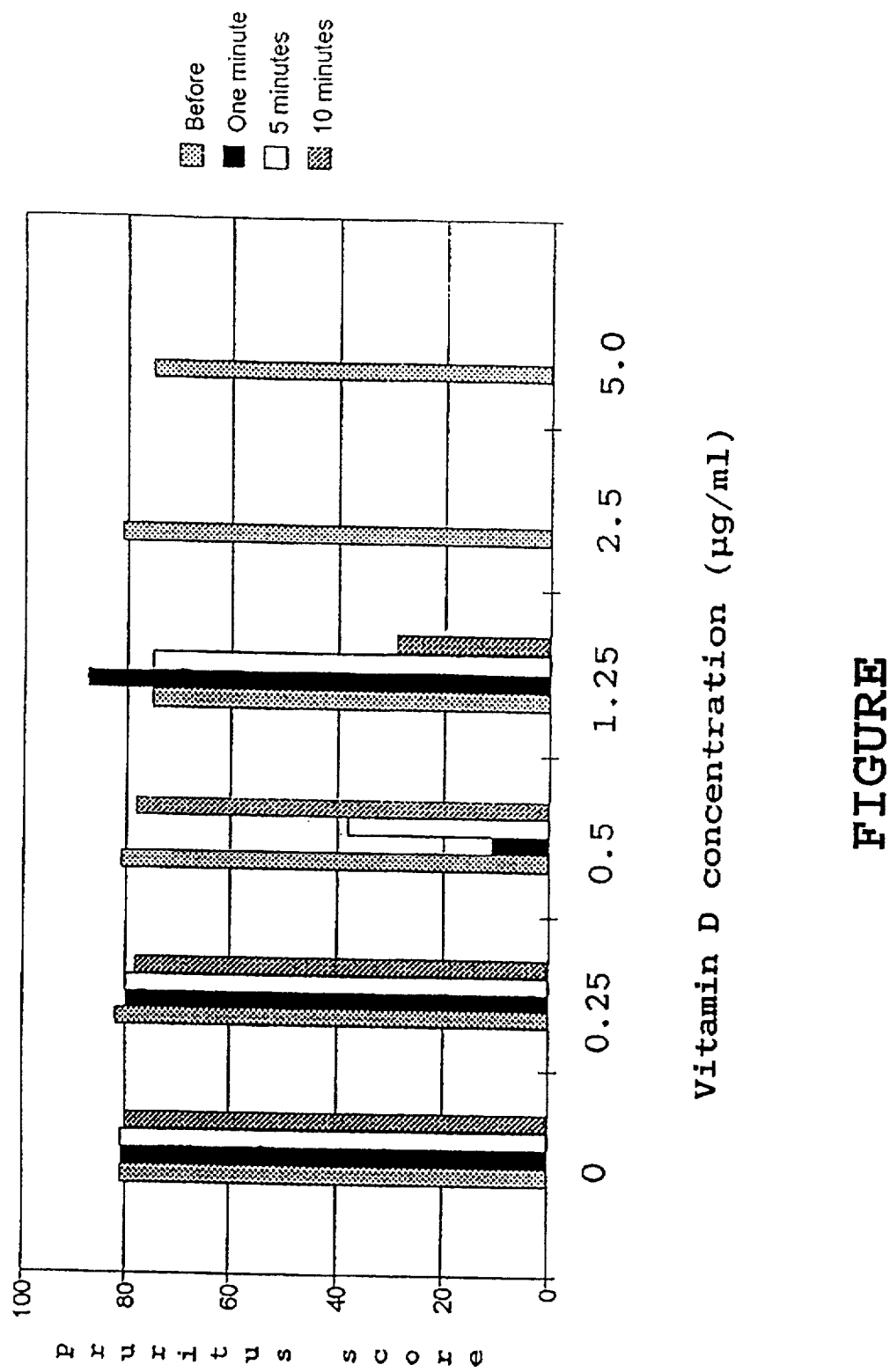
FIGURE

TREATMENT OF PRURITUS WITH VITAMIN D AND ANALOGS THEREOF

This application claims priority under 35 U.S.C. § 119(e) to provisional application No. 60/005,030 filed Oct. 10, 1995.

BACKGROUND OF THE INVENTION

(1) Field of the Invention

This invention relates generally to the field of treating pruritus and, more particularly, to the topical treatment of pruritus using vitamin D and analogs thereof.

(2) Description of the Related Art

Pruritus is a condition involving localized or general itching which can be mediated by stimulation of sensory nerve endings. Although usually occurring in the skin, pruritus can also occur in non-cutaneous sites such as mucous membranes or cornea. A variety of causes for the condition of pruritus are known including external and exogenous causes, localized skin disorders and systemic diseases.

The first line of treatment involves diagnosis of the underlying condition that causes the pruritus and intervening therapeutically to alleviate that underlying condition. Such therapeutic treatment is appropriate for example in the treatment of psoriasis with UV light or with topical vitamin $D_3$ analogs. These treatments are not considered to be direct treatments of the pruritus and only indirectly relieve the itching. Indeed, some treatment modalities for psoriasis can cause itching (for example, see product insert for the vitamin D analog Dovonex®, Westwood-Squibb). At the same time the underlying disease is being treated, it might also be desirable to directly treat the pruritus. Furthermore in some conditions involving pruritus, either the underlying cause for the pruritic condition cannot be determined or it cannot be eliminated. In such cases the direct treatment of the pruritic condition is required.

Currently available treatment modalities for pruritus include nonspecific topical agents such as emollients and counterirritants, topical drugs such as steroids, local anesthetics and antihistamines, and physical modalities such as ultraviolet phototherapy and thermal stimulation. Some of these treatments are effective in pruritic conditions of particular etiology, while others may show general but nonspecific benefit.

Nonspecific topical preparations can act as moisturizing lotions or creams or as oil-based ointments that are occlusive and serve to soften dry skin as well as providing a protective covering. These can sometimes contain chemical substances in the preparation which do not contribute to the nonspecific antipruritic action of the preparation and provide no antipruritic action themselves.

Topical formulations containing pharmacologically active agents are often useful in particular pruritic conditions but may not be generally useful in all pruritic conditions. For example, topical corticosteroids are not indicated for symptomatic treatment unless a steroid responsive disorder is diagnosed. Physical modalities such as UV light have been particularly effective in a variety of conditions although undesirable side effects can be produced by UV light such as an increased risk of developing skin cancer as well as undesirable phototoxic reactions (see for example, Marks, *J Dermatol Treat* 1:233–234, 1989)

Thus it would be desirable to develop new anti-pruritic agents that are effective in treating pruritus resulting from a wide variety of causes or that are able to alleviate pruritus produced by different causes than those that can be treated by currently available agents.

The ability of vitamin $D_3$ to effectively treat pruritus when administered in a topical treatment formulation has not been heretofore known. The effectiveness of UVB light therapy in the treatment of pruritus has been noted to be incidentally related to the production of vitamin D in the skin (Blachley et al., *Am J Kidney Dis* 5:237–241, 1985). The same wavelengths of between 290 and 310 nm used in UVB treatment is also able to photolyze provitamin $D_3$(7-dehydrocholesterol) which then internally isomerizes to form vitamin $D_3$. Nevertheless no direct link between vitamin $D_3$ production in the skin and the antipruritic effectiveness of UVB light treatment has been reported and, in addition, the mechanism of the therapeutic benefit of UVB light remains unknown.

Vitamin $D_3$ is also incidentally present in some formulations that are indicated to be useful in certain conditions involving itching. One such nonspecific topical preparation was reported in U.S. Pat. No. 3,711,602 issued to Herschler. This patent discloses a formulation containing lanolin, DMSO, isopropyl myristate, vitamin A and vitamin $D^3$ that is applied topically for the treatment of burns, skin irritation, diaper rash and pruritus. This preparation is nonaqueous and provides occlusion and physical soothing actions. It is believed, however, that the vitamin D present in the formulation at a concentration of 7.5 µg/ml does not directly contribute any anti-pruritic effect. This is because the lowest concentration found to have an anti-pruritic effect in a non-aqueous vehicle in the studies reported herein was 521 µg/ml.

Other preparations that serve as nonspecific, physically soothing formulations also sometimes contain vitamin D such as for example A and D® Ointment for soothing relief of diaper rash or Desitin® also used to sooth diaper rash including preventing the burning, pain and itch produced by irritants. These preparations, however, provide only a protective physical barrier to water and irritants and the vitamin D present in these preparations is incapable of producing any direct antipruritic action as a result of not being bioavailable from such formulations.

Thus, although vitamin $D_3$ has been incidentally related to some treatment modalities for pruritus, it has not heretofore been known that vitamin $D_3$ can be effectively used in the treatment of pruritic conditions.

SUMMARY OF THE INVENTION

In accordance with the present invention, it has been discovered that vitamin D can be applied topically in certain formulations that make the vitamin D bioavailable. Surprisingly, when administered in such formulations at pruritic sites, the vitamin D becomes therapeutically effective and the pruritus is rapidly and completely relieved.

Because vitamin D is a fat soluble substance, a water-based emulsion formulation that is bioavailable and suitable for topical treatment can be used. Thus, one formulation for vitamin D that is effective in treating pruritus comprises a mixture of water, a water-insoluble organic liquid, a surface active agent, and a vitamin D or an analog thereof. This formulation is effective when the vitamin D is present at a concentration as low as 2.5 µg/ml.

A second formulation that is also effective in treating pruritus is based upon a nonaqueous carrier vehicle for vitamin D. This formulation comprises a water-insoluble organic liquid such as petroleum or corn oil and vitamin D.

The vitamin D concentration in this formulation can be as low as 521 µg/ml.

Another vitamin D formulation effective in treating pruritus comprises a suspension of water and a dispersed phase containing vitamin D or analog thereof. This formulation is effective at concentration of 12.5 µg/ml.

Among the several advantages achieved by the present invention, therefore, may be noted the provision of new treatment for pruritus that is broadly effective in a variety of pruritic conditions; the provision of a treatment modality that is safe being neither irritating nor toxic; the provision of a treatment that is inexpensive; and the provision of a treatment that has a low potential for sensitizing the treatment site by virtue of its being an endogenous or closely related to an endogenous substance.

BRIEF DESCRIPTION OF THE DRAWING

The FIGURE illustrates the concentration-response relationship of the antipruritic effect of vitamin $D_3$ (0.25–5.0 µg/ml) in alleviating the itching produced by poison ivy.

DESCRIPTION OF THE PREFERRED EMBODIMENTS

The present invention is thus based upon the discovery that vitamin D can effectively treat pruritic conditions when administered topically in a therapeutically effective formulation. By a therapeutically effective formulation it is meant that the active substance is bioavailable, that is able to exert a biological activity when administered in that formulation. Such formulations effectively exhibit the biological activity of vitamin D in diminishing or completely alleviating the itching involved in pruritic conditions. The formulation is also pharmaceutically acceptable for topical application.

Vitamin D within the scope of this invention is intended to include vitamin $D_3$ or cholecalciferol as well as the several related steroids and their metabolites that are referenced in the art by the term vitamin D provided such compound show the biological activity of vitamin D. Thus vitamin D compounds include alfacalcidol, calcifedol, calcitriol, cholecalciferol, dihydrotachysterol, and ergocalciferol (Martindale, *The Extra Pharmacopoeia* 30th Ed., Martindale, 1993, pp. 1058–1059).

Also included within the scope of this invention and within the meaning of the term vitamin D are analogs of vitamin D. Analogs of vitamin D are well known in the art and such compounds can have modifications in the side chain and/or changes in the nuclear part of the secosteroid molecule. Vitamin D analogs can contain side chain modifications involving introduction of unsaturation; transposing, adding, removing or substituting hydroxyl groups; substituting hydrogens; forming carbocyclic structure; introducing a heteroatom link; inverting stereochemically; removing or adding alkyl groups and changing the number of links in the side chain. (see Calverly and Jones, in *Antitumor Steroids* blickenstagg, Ed., Academic Press, Inc., San Diego, 1992, 193–270 which is incorporated by reference). All of these compound are thus included in the term vitamin D so long as they exhibit the biological activity of antipruritic effectiveness in a bioavailable formulation. Such biologically active vitamin D compounds may not show the same degree of activity as vitamin $D_3$, but need only show at least some discernable antipruritic effect.

One embodiment of the present invention is an aqueous-based emulsion formulation comprising water, a water-insoluble organic liquid, a surface active agent and vitamin D. The surface active agent is biocompatible and suitable for application by topical formulation. The formulation also contains a biocompatible water-insoluble organic liquid such as an oil or lipid suitable for forming an oil-in-water or water-in-oil emulsion so that the formulation is a cream, ointment, paste or the like. By biocompatible it is meant that the substance produces no untoward biological effects such as local or generalized toxic effects or local irritation at the site of topical application. Suitable water-insoluble organic liquids are well known in the art field of topically applied cosmetics and therapeutics and include but are not limited to mineral oil, corn oil or other vegetable oil, petroleum, lanolin, fish oil and the like.

The use of surface active agents in preparations that are topically applied is well known particularly in the field of cosmetics (for example see *Surfactants in Cosmetics*, Rieger, M., Ed., Marcel Dekker, Inc., N.Y., 1985 which is incorporated by reference). Thus, a number of biocompatible surface active agents can be used in the present invention including but not limited to (1) anionic surfactants such as monovalent or polyvalent carboxylate salts, acyl lactylates, alkyl ether carboxylates, N-Acyl Sarcosinates, N-Acyl Glutamates, fatty acid-polypeptide condensates, sulfuric acid esters including alkyl sulfates and ethoxylated alkyl sulfates, ester-linked sulfonates, alpha olefin sulfonates, phosphated ethoxylated alcohols; (2) cationic surfactants such as monoalkyl quaternary ammonium salts, dialkyl quaternary ammonium compounds, amidoamines and aminimides; (3) amphoteric surfactants such as N-substituted alkyl amides, N-alkyl betaines, sulfobetaines, and N-alkyl beta-aminopropionates; and (4) nonionic surfactants such as (a) polyoxyethylene compounds including ethoxylated alcohols, ethoxylated esters and ethoxylated amines; (b) polyoxypropylene compounds such as propoxylated alcohols, ethoxylated/propoxylated block polymers and propoxylated esters; (c) alkanolamines; (d) amine oxides; and (e) fatty acid esters of polyhydric alcohols such as ethylene glycol esters, diethylene glycol esters, propylene glycol esters, glyceryl esters, polyglyceryl fatty acid esters, sorbitan esters, sucrose esters and glucose esters.

The selection of a particular surface active agent would depend upon a number of factors including but not limited to the particular causation agent for the pruritic condition and whether topical lesions accompany the pruritic condition. The formulations of the present invention are useful in treating pruritic conditions on the skin, mucous membranes or cornea. Selection of a suitable surface active agent can thus be based in part on the site being treated. For example, amphoteric or nonionic surface active agents known in the art are selected for uses in and around the eyes to avoid corneal irritation. One skilled in the art can readily select a surface active agent and formulation suitable for a particular site and pruritic condition as well as for other factors.

In another embodiment of the present invention a water-insoluble formulation is provided comprising a biocompatible, water-insoluble organic liquid such as a biocompatible oil or lipid suitable as a carrier for the vitamin D. The carrier must be suitable in the sense of being compatible with the vitamin D and any other ingredients and not deleterious to the patient being treated. Suitable organic liquids include petroleum jelly, corn oil or other vegetable oil, mineral oil, lanolin, fish oil and the like.

The Vitamin D compounds of the present invention can also be formulated into bioavailable suspensions or dispersions such as, for example, hydrosols and hydrogels in which a true emulsion is not formed. The formulation is a mixture of two or more substances forming a dispersed phase which is finely divided and uniformly distributed through a dispersion medium which is usually water. The dispersed phase can be a solid or an oil phase with stabilizers to form a stabilized colloidal system. Suspending or dispersing agents may also be added to the formulation and can include surface active agents capable of stabilizing the suspension or dispersion. The preparation of suspensions and ingredients used in the formation of suspensions are well known in the art and one skilled in the art can readily prepare such suspension.

In addition to the above ingredients, the formulations of this invention may also include one or more additional auxiliary ingredients such as diluents, buffers, or preservatives such as methyl hydroxybenzoate and/or anti-oxidants and the like. Such additional ingredients can also be pharmaceutically-acceptable excipients for modifying or maintaining the pH, osmolarity, viscosity, clarity, color, sterility, stability, rate of dissolution, or odor of the formulation. Similarly, the formulation may contain still other pharmaceutically-acceptable excipients for modifying or maintaining release or absorption or penetration of the site by the vitamin D compound. Moreover, other therapeutic substances can be incorporated into the formulation such as, for example, other antipruritic agents, vitamins, antifungals, antiinflammatory agents, antibiotics, sunscreens and the like.

The topical formulations described herein can be used in treating virtually any pruritic site such as for example on the skin, mucous membranes or cornea. Such treatments include scalp treatment as in shampoos, conditioners and the like, rectal treatment, eye treatment, treatment of nasal membranes, treatment of the ear canal, etc.

The formulations in the present invention are intended for use in treating a wide variety of pruritic conditions in humans as well as in non-human mammals, birds, reptiles, amphibians and fish. Conditions that are intended for treatment by the present invention include but are not limited to chickenpox, shingles, plant toxins such as poison ivy, insect bites, chronic kidney failure, liver diseases such as primary biliary cirrhosis and alcoholic cirrhosis, malabsorption syndromes such as steatorhea, HIV infection, AIDS related eosinophilic pustular folliculitus, psoriasis, atopic dermatitis, photosensitivity disorders, lichen planus, polycythemia vera, Grover's disease, glanuloma annulare, lichen nitidus, prurigo nodularis, macular amyloidosis, urticaria pigmentosa, aquagenic pruritus, pemphigus vulgarus, lupis vulgaris, healing cuts and burns, senile pruritus, hypereosinophilic syndrome, chronic uticaria, pruritic eye conditions, and stress.

Preferred embodiments of the invention are illustrated in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates antipruritic effect of vitamin $D_3$ in Vita Moist Hand and Nail Cream in the alleviating the pruritus of chickenpox.

Having becoming ill with chickenpox, I developed severe pruritus. I applied the commercially available skin cream, Vita Moist Hand and Nail Cream (Avon, N.Y.) hereinafter referenced as Vita Moist Cream and the pruritus was completely and immediately alleviated. The effect of the cream lasted for several hours and when the itching returned, I reapplied the cream with the result that the pruritus was again completely and immediately alleviated.

Vita Moist Cream is sold as a skin moisturizer and carries no indication for use in treating pruritus. Upon reviewing the medical literature, I learned that UVB light was effective in treating pruritic conditions and that, incidentally, UVB light also produces vitamin $D_3$. I concluded that vitamin $D_3$ was likely to be the active ingredient in Vita Moist Cream. As commercially available, Vita Moist Cream contains 10 µg/ml vitamin $D_3$ among other ingredients. Ingredients present in Vita Moist Cream are as follows:

| VITA MOIST CREAM | |
| --- | --- |
| A | Purified Water |
| E | Glycol Stearate |
| E | Glycerin |
| E | Isopropyl Palmitate |
| E | Dimethicone |
| E | Myristyl Myristate |
| E | Peg-40 Stearate |
| E | Stearyl Alcohol |
| E | Steareth-2 |
| E | Mineral Oil |
| F | Methylparaben |
| F | Imidazolidinyl Urea |
| F | Triethanolamine |
| F | Fragrance |
| F | Carbomer-934 |
| .02000 | Retinyl Palmitate |
| .02000 | Tocopheryl Acetate |
| G | Corn Oil |
| G | Hydrolyzed Animal Keratin |
| G | Propylene Glycol |
| G | SD Alcohol 40-B |
| .00100 | Cholecalciferol |
| G | Disodium EDTA |
| G | FD & C Yellow No. 5 |
| G | FD & C Red No. 4 |
| G | EXT D & C Violet No. 2 |

A = MORE THAN 50%
E = MORE THAN 5%
F = .1% TO 1%
G = LESS THAN .1%

EXAMPLE 2

This example illustrates the antipruritic effect of vitamin $D_3$ formulated in corn oil for alleviating the pruritus of sunburn.

A corn oil solution of vitamin $D_3$ was prepared by adding 1 gram of vitamin $D_3$ to 20 ml corn oil with mixing for approximately 1 hour followed by brief heating to approximately 45° C. until dissolved. One ml of this solution was mixed with 47 ml corn oil and 2 ml isopropyl myristate to obtain a final concentration of vitamin $D_3$ of 1000 µg/ml.

Subject CS developed a sunburn on the back and experienced severe pruritus. Application of Vita Moist Cream provided some but incomplete relief. An intense pruritus returned and was then dealt by applying 1000 µg/ml in corn oil with the result that the prutitus was immediately and completely alleviated. Approximately an one and one-half hours later, the pruritus returned and was alleviated by multiple applications of Vita Moist Cream, vitamin $D_3$ at 1000 µg/ml in corn oil, and constant massaging. The pruritus abated completely about one-half hour after these applications.

EXAMPLE 3

This example illustrates the antipruritic effect of vitamin $D_3$ formulated in water-based emulsions in alleviating the pruritus caused by poison ivy.

Water-based Emulsion Formulations

Water-based emulsions were prepared using Keri® lotion (Bristol-Meyers Squibb Co., NY) and Eucerin® lotion (Beiersdorf, Inc., Norwalk, Conn.).

Keri® lotion has the following composition as indicated on the container label.

| KERI ® LOTION |
| --- |
| Water |
| Petroleum |
| Glycerin |
| Dimethicone |
| Steareth-2 |
| Cetyl Alcohol |
| Benzyl Alcohol |
| Laureth-23 |
| Magnesium Alimunim Silicate |
| Tocopheryl Linoleate |
| Carbomer |
| BHT |
| Sodium Hydroxide |
| Disodium EDTA |
| Quaternium-16 |

Eucerin® lotion has the following composition as indicated on the container label.

| EUCERIN ® LOTION |
| --- |
| Water |
| Mineral Oil |
| Isopropyl Myristate |
| PEG-40 Sorbitan Peroleate |
| Glyceryl Lanolate |
| Sorbitol |
| Propylene Glycol |
| Cetyl Palmitate |
| Magnesium Sulfate |
| Aluminum Sterate |
| Lanolin |
| Alcohol |
| BHT |
| Methylchloroisothiazolinone |
| Methylisothiazolinone |

Keri® lotion preparations were made containing various concentrations of vitamin $D_3$ by mixing stock solutions as indicated below and heating the mixture at 46°–50° C. with occasional stirring. 869 µg/ml: One ml of the 5% solution of vitamin $D_3$ from example 2 was mixed with 2 ml corn oil to obtain 16,666 µg/ml solution. 0.55 ml of this solution was then mixed with ten ml of Keri® lotion. 521 µg/ml: 0.55 ml of vitamin $D_3$ in corn oil at 10,000 µg/ml as described above was added to 10 ml Keri® Lotion. 502 µg/ml: 0.55 ml of the 10,000 solution of was mixed with 10 ml Keri® Lotion and 0.4 ml isopropyl myristate. 52 µg/ml: 0.55 ml of 1,000 µg/ml stock solution, prepared by mixing 1 ml of 5% vitamin $D_3$ stock with 2 ml isopropyl myristate and 47 ml corn oil, was added to 10 ml Keri® Lotion. 10 µg/ml: 0.55 ml of 200 µg/ml stock solution, prepared by mixing 1 ml of 5% vitamin $D_3$ stock with 49 ml corn oil and subsequently diluted 1:5 in corn oil, was added to 0.4 ml isopropyl myristate and 10 ml Keri® Lotion.

Eucerin® lotion preparation at 869 µg/ml was made as described above for Keri® lotion.

Vita Moist Cream had the composition as shown in example 1.

As placebo control Care Deeply Hand and Nail Cream (Avon, N.Y.) hereinafter referenced as Care Deeply, has the following composition:

| CARE DEEPLY HAND AND NAIL CREAM |
| --- |
| Purified Water |
| Glycerin |
| Cocoa Butter |
| Cetearyl Alcohol |
| Isopropyl Myristate |
| Emulsifying Wax |
| Ceteareth-20 |
| Isopropyl Lanolate |
| Choleth-24 |
| Glycol Stearate |
| Methylparaben |
| Lanolin Oil |
| Imidazolidinyl Urea |
| Carbomer-941 |
| Dimethicone |
| Magnesium Aluminum Silicate |
| Triethanolamine |
| Fragrance |
| Tetrasodium EDTA |
| FD & C Yellow No. 5 |
| FD & C Red No. 4 |
| FD & C Blue No. 1 |

Testing Procedure

Subject MS contracted poison ivy rash and tested the various preparations above. Preparations were evaluated by the subject after application to an area of rash approximately 1–10 square centimeters. Comparisons were made of antipruritic effect by marking on a 100 mm visual analog scale consisting of a plain line with the left end labeled "None" and the right end labeled "Maximal". The subject was instructed to mark the scale at a point which she felt corresponded to the level of itchiness that she was feeling at the treatment site at the appropriate time. The samples were coded so that the subject was not aware of what a given sample was and she was not told if they were expected to have an effect. She carried out the evaluation unaided, applying the samples in any order she chose except where side-by-side comparisons were made as indicated in the tables. From the marked scale the pruritic score was determined as the number of mm from the left side of the scale to the subject's mark. Thus a higher value indicates a high level of pruritus and a low value indicates a low level to no pruritus. Tables 1a through 1c show the antipruritic effect of water-based emulsion preparations.

Table 1a shows an antipruritic effect of Vita Moist Cream containing vitamin $D_3$ at 10 µg/ml compared to the control cream, Care Deeply. The pruritus was completely alleviated one minute after application.

TABLE 1a

| VITA MOIST (Vitamin D3 - 10 µg/ml)* | | |
| --- | --- | --- |
| Time (min) | Care Deeply Control | Vita Moist ($D_3$-10 µg/ml) |
| 0 | 81 | 81 |
| 1 | 75 | 0 |
| 5 | 74 | 0 |
| 10 | 76 | 0 |

*Side-by-side comparison was made.

In Table 1b, it is seen that Keri® lotion as a vehicle for vitamin $D_3$ also produces a rapid and complete antipruritic effect as was seen in Table 1a for Vita Moist Cream. Also, it is seen that the addition of isopropyl myristate to the formulation did not effect the antipruritic effect of vitamin $D_3$.

TABLE 1b

KERI LOTION (containing Vitamin $D_3$)

| Time (min) | 10 | 10 | 10* | 10* | Mean |
|---|---|---|---|---|---|
| 0 | 80 | 77 | 78 | 80 | 79 |
| 1 | 1 | 0 | 0 | 0 | 0 |
| 5 | 0 | 0 | 0 | 0 | 0 |
| 10 | 0 | 0 | 0 | 0 | 0 |

*Preparation conatined no Isopropyl Myristate.

Table 1c shows that concentrations of vitamin $D_3$ from 10 through 869 µg/ml are effective in rapidly and effectively relieving pruritus.

TABLE 1c

KERI LOTION (with added Isopropyl Myristate)

| Time (min) | Vitamin $D_3$ Concentrations | | | | | |
|---|---|---|---|---|---|---|
| | 0 | 10** | 52 | 502 | 521* | 869 |
| 0 | 82 | 79 | 77 | 80 | 80 | 82 |
| 1 | 66 | 0 | 35 | 0 | 81 | 0 |
| 5 | 47 | 0 | 0 | 0 | 0 | 0 |
| 10 | 25 | 0 | 0 | 0 | 0 | 0 |

**Mean values from Table 1b.
*Preparation contained no Isopropyl Myristate.

The formulation of 869 µg/ml vitamin $D_3$ in Eucerin® was compared with a Eucerin® control vehicle prepared from Eucerin® with an added amount of corn oil identical to that in the active formulation but containing no vitamin $D_3$. No scores were recorded, however, the subject indicated that the Eucerin®-vitamin $D_3$ preparation stopped the pruritus instantly and completely whereas the control had no antiprutitic effect.

EXAMPLE 4

This example illustrates the antipruritic effect of vitamin $D_3$ formulated in oil-based preparations in alleviating the pruritus caused by poison ivy.

A petroleum jelly formulation was prepared as follows. One gram of vitamin $D_3$ was dissolved in 20 ml corn oil as described in example 2. One ml of the resultant 5% solution was mixed with 4 ml corn oil to obtain a 10,000 µg/ml solution. Ten ml of petroleum jelly was then mixed with 0.55 ml of the 10,000 µg/ml solution upon heating to 50°–55° C. to give a resultant concentration of 521 µg/ml. Placebo control was made by adding 0.55 ml corn oil to 10 ml petroleum jelly.

The corn oil formulation was prepared by adding 1 ml of the 5% stock solution of vitamin $D_3$ in 2 ml isopropyl myristate and 47 ml corn oil to give a final concentration of 1000 µg/ml.

Vitamin A and D Ointment (Schering-Plough, Memphis, Tenn.) contained the label-indicated ingredients of vitamin A at 1856 I.U./g and vitamin D at 270 I.U./g or 6.75 µg/ml in white petrolatum and zinc oxide.

The patient and test procedures were as described in example 3. The results of tests using oil-based formulations are in tables 2a through 2c.

In Table 2a it is seen that corn oil as a vehicle for vitamin $D_3$ at 1000 µg/ml produced no detectable antipruritic effect when the mean of two tests were compared to vehicle control. In contrast, Table 2b showed an antipruritic effect for vitamin $D_3$ at a concentration of 521 µg/ml in the vehicle, petroleum jelly. The commercial product, A and D ointment shown in Table 2c showed no antipruritic effect.

TABLE 2a

CORN OIL

| Time (min) | Control | | | Vitamin D (1000 µg/ml) | | |
|---|---|---|---|---|---|---|
| | 1 | 2 | Mean | 1 | 2 | Mean |
| 0 | 82 | 82 | 82 | 80 | 81 | 81 |
| 1 | 81 | 48 | 65 | 80 | 81 | 81 |
| 5 | 81 | 12 | 47 | 81 | 58 | 70 |
| 10 | 83 | 2 | 43 | 60 | 58 | 59 |

TABLE 2b

PETROLEUM JELLY

| Time (min) | Control | Vitamin $D_3$ (521 µg/ml) |
|---|---|---|
| 0 | 80 | 72 |
| 1 | 79 | 11 |
| 5 | 78 | 10 |
| 10 | 58 | 9 |

TABLE 2c

A AND D OINTMENT*

| Time (min) | Petroleum Jelly | | | A and D Ointment ($D_3$-6.75 µg/ml) | | |
|---|---|---|---|---|---|---|
| | 1 | 2 | Mean | 1 | 2 | Mean |
| 0 | 81 | 68 | 75 | 81 | 58 | 70 |
| 1 | 81 | 2 | 42 | 1 | 61 | 31 |
| 5 | 0 | 0 | 0 | 80 | 61 | 71 |
| 10 | 0 | 43 | 22 | 82 | 52 | 67 |

*A side-by-side comparison was made.

EXAMPLE 5

This example illustrates the antipruritic effect of vitamin $D_3$ formulated in a water-based suspension in alleviating the pruritus caused by poison ivy.

Vita Moist Cream was used as control reference formulation and this had the composition as shown in example 1. Vita Moist Body Lotion (Avon, N.Y.), is a commercially available aqueous suspension formulation containing vitamin $D_3$. This composition contains the following ingredients.

| VITA MOIST BODY LOTION | |
|---|---|
| A | Purified Water |
| E | Stearic Acid |
| E | Hydrogenated Soybean Oil |
| E | Glycerin |
| E | Squalane |

-continued

VITA MOIST BODY LOTION

| | |
|---|---|
| F | Cetyl Acetate |
| F | Triethanolamine |
| F | Glyceryl Stearate |
| F | Sesame Oil |
| F | Methylparaben |
| F | Magnesium Aluminum Silicate |
| F | Fragrance |
| F | Propylparaben |
| F | Acetylated Lanolin Alcohol |
| .05000 | Tocopheryl Acetate |
| .02500 | Retinyl Palmitate |
| F | Corn Oil |
| F | BHT |
| F | Propylene Glycol |
| F | SD Alcohol 40-B |
| .00125 | Cholecalciferol |
| F | BHA |
| F | Disodium EDTA |
| F | FD & C Yellow No. 5 |
| F | FD & C Red No. 4 |
| F | EXT D & C Violet No. 2 |

A = MORE THAN 50%
E = FROM 1% TO 5%
F = .1% TO 1%
G = LESS THAN .1%

The patient and test procedures were as described in example 3. The results of tests using oil-based formulations are in Table 3.

TABLE 3

VITAMIN $D^3$ SUSPENSION (VITA MOIST LOTION)

| Time (min) | Vita Moist Cream ($D_3$-10 µg/ml) | | | Vita Moist Lotion ($D_3$-12.5 µg/ml) | | |
|---|---|---|---|---|---|---|
| | 1 | 2 | Mean | 1 | 2 | Mean |
| 0 | 70 | 79 | 74 | 71 | 78 | 74 |
| 1 | 0 | 78 | 39 | 49 | 78 | 64 |
| 5 | 0 | 0 | 0 | 11 | 56 | 34 |
| 10 | 0 | 0 | 0 | 3 | 5 | 4 |

As reported in example 3, Vita Moist Cream again completely alleviated the pruritus, although in this test, complete effectiveness was seen at the 5 minute observation rather than at the 1 minute observation in example 3. In comparison to this, Vita Moist Lotion only partially alleviation of the pruritis at 5 minutes and nearly complete relief was obtained by 10 minutes. Thus the suspension preparation appeared to be less rapid in producing the antipruritic effect than was the emulsion preparation, Vita Moist Cream.

EXAMPLE 6

This example illustrates the dose-response relationship of Vitamin $D_3$ in a water-based emulsion vehicle prepared by mixing Vita Moist Cream containing Vitamin $D_3$ with Care Deeply Cream which contains no Vitamin $D_3$.

Serial dilutions of Vita Moist Cream were made from an initial 5 ml quantity of Vita Moist Cream by adding successive 5 ml quantities of the diluent, Care Deeply Cream, to the starting formulation and subsequent 5 ml aliquots of successive dilutions as follows:

1. 5 ml Vita Moist+5 ml diluent—5.0 µg/ml
2. 5 ml of 5 µg/ml+5 ml diluent—2.5 µg/ml
3. 5 ml of 2.5 µg/ml+5 ml diluent—1.25 µg/ml
4. 5 ml of 1.2 µg/ml+5 ml diluent—0.5 µg/ml
5. 5 ml of 0.5 µg/ml+5 ml diluent—0.25 µg/ml
6. 5 ml diluent After coding with numbers 1–6 as above, the preparations were randomly sorted and again coded A–E and tested two at a time in alphabetical order. The results are shown in the FIGURE. As can be seen concentrations of 2.5 and 5 µg/ml produced rapid and complete alleviation of pruritus. The concentrations of 1.25 µg/ml and 0.5 µg/ml produced some antipruritic effect but the effect was not complete nor was it rapid and sustained. The minimal effective concentration in this formulation appears to be between 1.25 and 2.5 µg/ml.

EXAMPLE 7

The following example illustrates the clinical testing of vitamin D formulations in patients having uremic pruritus.

In this study, vitamin D formulations will be tested against placebo. The vitamin D preparations will be based upon the formulations discussed above. The placebo will contain only the formulation without vitamin D.

The study would be double blind, meaning that both the nurse and the patient will be unaware of which cream contains the test material and which contains only placebo. The containers will be coded so that only the attending physician will know which is which. The code may be different from one formulation set to the next.

The nurse protocol is as follows:

The patient must be suffering from chronic kidney failure and be experiencing bothersome itchiness at the time of the office visit. The patient will be asked if they would like to volunteer to try this new treatment. It will be explained that this is a trial of a cream that relieves itchiness in chickenpox and poison ivy and that it may or may not help them.

The patient will be assisted in understanding and completing the questionnaire. If needed, the nurse can assist by writing the answers given by the patient. The questionnaire is as follows:

| Cream Number |
|---|
| 1. Patient's name and phone number. |
| 2. Date and time. |
| 3. Age/Sex. |
| 4. Date when dialysis was started. |
| 5. What kind of renal disease do you have? |
| 6. Do you have a history of persistent itchiness? If so, for how long? |
| 7. Is your itchiness constant or does it come and go? If it's not constant, when is it usually the worst? |
| 8. Are you itching right now? |
| 9. Do you have itchiness all over your body or only on part of your body? If only on part of your body, please indicate where. |
| 10. What treatments have you tried to reduce the itchiness and which have been the most effective? |
| Nurses' comments (to be filled out after evaluation): |
| Follow up comments: |
| Nurses' signature |
| Doctors' signature |

Chose the sites to apply the creams based on where the itching is most severe. Apply creams "X" and "O" to areas of roughly equal size and itchiness. Indicate under "Nurses' comments" where the creams were applied. If the itching is general, use one forearm for the test cream and the other forearm for the placebo cream. The cream should soak in completely. If it doesn't, you put too much on. If the patient has an adverse reaction to the cream, stop the trial and remove the cream immediately.

If one of the creams relieves the itching, let them apply the cream to all of the affected areas of skin after the trial is completed before leaving the office. Ask the patient to make a note of when the itchiness returns and explain that you will make a follow up call ask how long the treatment lasted. Do not give any extra to take home. Explain that the attending physician is barred by law to prescribe or dispense it.

Please indicate under "Nurses' comments" if there is anything about the patient that you think we should know when reviewing the questionnaire. This could include problems other than uremia that could cause pruritus.

Treatment is evaluated by the patient as discussed in Example 3 above. The patient is instructed as to how to mark the 100 mm visual scale from "None" to "Maximal" pruritus. The scale is explained with no suggestion as to where the mark should be placed. Only the patient will decide where to place the mark.

The evaluation sheet is as follows:

---

Patient's name and date:

TREATMENT EVALUATION

Please indicate how serious the itchiness is using the following scales. make a mark on the line at the point that you feel corresponds to the severity of the itchiness that you are experiencing at the treatment sites for each appropriate time. Slight itchiness would be indicated by making a mark near the left side of the scale while severe itchiness would be indicated by making a mark near the right side of the scale. Maximal itchiness means the most severe itchiness that you can imagine.

BEFORE APPLICATION

| Site X NONE | MAXIMAL |
| Site O NONE | MAXIMAL |

ONE MINUTE AFTER APPLICATION

| Site X NONE | MAXIMAL |
| Site O NONE | MAXIMAL |

FIVE MINUTES AFTER APPLICATION

| Site X NONE | MAXIMAL |
| Site O NONE MAXIMAL | |

TEN MINUTES AFTER APPLICATION

| Site X NONE | MAXIMAL |
| Site O NONE | MAXIMAL |

Please describe in your own words the effect of the cream on the itchiness.
If this treatment is effective, we will call you for a follow up assessment to find out how long the treatment is effective. Please try to note when the itchiness returns. Thank you very much!

---

Approximately 10 patients will be used in the study and each patient will receive both vitamin D treatment formulation and placebo. Data will be collected and statistical comparison will be made between effects of the formulation and effects of placebo.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for treating pruritus comprising topically administering an antipruritic effective amount of a vitamin D compound or an analog thereof in a therapeutically effective formulation which lacks dimethyl sulfoxide and is pharmaceutically acceptable for topical application, wherein the therapeutically effective formulation is an emulsion comprising water, a water-insoluble organic liquid, a surface active agent, and the vitamin D compound or analog thereof.

2. The method according to claim 1 wherein the vitamin D compound is selected from the group consisting of alacalcidol, calcifediol, calcitriol, cholecalciferol, dihydrotachysterol and ergocalciferol.

3. The method according to claim 1 wherein the analog of vitamin D comprises a vitamin D compound having sidechain modifications, said modifications being made by introduction of unsaturation; transposing, adding, removing or substituting hydroxyl groups; substituting hydrogens; forming carbocyclic structure; introducing a heteroatom link; inverting stereochemically; removing or adding alkyl groups; or changing the number of links in the side chain.

4. The method according to claim 1 wherein the surface active agent is selected from the group consisting of PEG-40 stearate, steareth-2, PEG-40 sorbitan peroleate, laureth-23 and combinations thereof.

5. The method according to claim 4 wherein the therapeutically effective formulation comprises at least about 50% water, from about 1 to about 5% PEG-40 stearate, from 1 to about 5% steareth-2 and cholecalciferol at a concentration of about 10 µg/ml.

6. The method according to claim 5 wherein the therapeutically effective formulation comprises cholecalciferol at a concentration of at least about about 2.5 µg/ml.

7. The method according to claim 6 wherein the pruritus results from a condition selected from the group consisting of chickenpox, shingles, plant toxins, insect bites, chronic kidney failure, liver diseases, malabsorption syndromes, HIV infection, AIDS related cosinophilic pustular folliculitis, psoriasis, atopic dermatitis, photosensitivity disorders, lichen planus, polycythemia vera, Grover's disease, glanuloma annular, lichen nitidus, prurigo nodularis, macular amyloidosis, urticaria pigmentosa, aquagenic pruritus, pemphigus vulgarus, lupis vulgaris, healing cuts and burns, senile pruritus, hypereosinophilic syndrome, chronic uticaria, pruritic eye conditions, stress, and combinations thereof.

\* \* \* \* \*